United States Patent
Elewaut et al.

(10) Patent No.: US 10,479,832 B2
(45) Date of Patent: Nov. 19, 2019

(54) METHOD OF TREATING BONE DISEASE

(71) Applicants: Universiteit Gent, Ghent (BE); VIB VZW, Ghent (BE)

(72) Inventors: Dirk Elewaut, Heusden (BE); Els Louagie, Torhout (BE); Nele Juchtmans, Ghent (BE)

(73) Assignees: Universiteit Gent, Ghent (BE); VIB VZW, Ghent (BE)

( * ) Notice: Subject to any disclaimer, the term of this patent is extended or adjusted under 35 U.S.C. 154(b) by 0 days.

(21) Appl. No.: 15/129,792

(22) PCT Filed: Mar. 30, 2015

(86) PCT No.: PCT/EP2015/056898
§ 371 (c)(1),
(2) Date: Sep. 27, 2016

(87) PCT Pub. No.: WO2015/150326
PCT Pub. Date: Oct. 8, 2015

(65) Prior Publication Data
US 2017/0129953 A1    May 11, 2017

(30) Foreign Application Priority Data
Mar. 31, 2014  (EP) ................................ 14162584

(51) Int. Cl.
*C07K 16/28*    (2006.01)
*A61K 39/00*    (2006.01)
*A61K 38/22*    (2006.01)

(52) U.S. Cl.
CPC .... *C07K 16/2803* (2013.01); *A61K 2039/505* (2013.01); *C07K 2317/73* (2013.01)

(58) Field of Classification Search
None
See application file for complete search history.

(56) References Cited

U.S. PATENT DOCUMENTS

2009/0104147 A1* 4/2009 Delputte .............. A61K 47/646
424/85.2

FOREIGN PATENT DOCUMENTS

| EP | 2206727 | 7/2010 |
|---|---|---|
| WO | 9806733 | 2/1998 |
| WO | 0112646 | 2/2001 |
| WO | 2008093166 | 8/2008 |
| WO | 2008142164 | 11/2008 |
| WO | 2010066740 | 6/2010 |
| WO | 2015150326 | 10/2015 |

OTHER PUBLICATIONS

Baum et al. (2016, Clinic. Rev. Allerg. Immunol. 51:1-15).*
SIGLEC1 Gene (Protein Coding) Sialic Acid Binding Ig Like Lectin 1 (visited Nov. 7, 2017) <http://www.genecards.org/cgi-bin/carddisp.pl?gene-SIGLEC1>.
Crocker et al., Siglecs and their roles in the immune system, Nature Reviews, Immunology, Apr. 2007, pp. 255-266, vol. 7, Nature Publishing Group.
Delputte et al., Porcine Sialoadhesin (CD169/Siglec-1) Is an Endocytic Receptor that Allows Targeted Delivery of Toxins and Antigens to Macrophages, PLoS ONE, Feb. 2011, vol. 6, Issue 2, twelve pages.
Hartnell et al., Characterization of human sialoadhesin, a sialic acid binding receptor expressed by resident and inflammatory macrophage poputations, Blood, Jan. 1, 2001, pp. 288-296, vol. 97, No. 1, The American Society of Hematology.
PCT International Search Report dated May 29, 2015, PCT/EP2015/056898.
Feng Xue et al, Detection of significant pathways in osteoporosis based on graph clustering, Molecular Medicine Reports, Sep. 13, 2012, pp. 1325-1332, vol. 6.
Catagni et al., Treatment of Massive Tibial Bone Loss Due to Chronic Draining Osteomyelitis: Fibula Transport Using the Ilizarov Frame, Orthopedics, Aug. 2007, vol. 30, Issue 8, three pages.
PCT Written Opinion dated May 29, 2015, PCT/EP2015/056898.
Ducreux et al., The Inhibitory Potencies of Monoclonal Antibodies to the Macrophage Adhesion Molecule Bialoadhesin Are Greatly Increased Following PEGylation. Bioconjug Chem. Europe PMC Funders Author Manuscripts, Oct. 2008; 19(10): 2088-2094. doi:10.1021/bc800259z.
Brahim, et al., The Malnutrition-Related Increas in Early visceralization of Leishmania donovani Is Associated with a Reduced Number of Lymph Node Phagocytes and Altered Conduit System Flow. PLos Neglected Tropical Diseases. Queensland Institute of Medical Research, Australia. 7(8): e2329. doi:10.1371/journal.ptnd.0002329.

* cited by examiner

*Primary Examiner* — Elizabeth C. Kemmerer
(74) *Attorney, Agent, or Firm* — Patent Law Works LLP

(57) ABSTRACT

The disclosure provides compositions and methods comprising a sialoadhesin binding moiety for treating metabolic and genetic bone disease, especially for treating a bone disorder of hyper-resorption of bone and/or enhanced activation of osteoclasts.

5 Claims, 13 Drawing Sheets

WT  KO

WT

KO sham WT OVX WT sham KO OVX KO

PBS mSn
mAb

METHOD OF TREATING BONE DISEASE

CROSS-REFERENCE TO RELATED APPLICATIONS

This application is a national phase entry under 35 U.S.C. § 371 of International Patent Application PCT/EP2015/056898, filed Mar. 30, 2015, designating the United States of America and published in English as International Patent Publication WO 2015/150326 A1 on Oct. 8, 2015, which claims the benefit under Article 8 of the Patent Cooperation Treaty to European Patent Application Serial No. 14162584.8, filed Mar. 31, 2014.

TECHNICAL FIELD

The application provides compositions and methods comprising a sialoadhesin binding moiety for treating metabolic and genetic bone disease, especially for treating a bone disorder related to aberrant osteoclast activity.

BACKGROUND

Remodeling (turnover) of bone is the process by which the adult skeleton is continually being resorbed (removed) and formed (replaced). Bone remodeling involves the synthesis of bone matrix by osteoblasts and its resorption by osteoclast cells. Both cell types are controlled by osteocytes that express and/or secrete M-CSF, RANKL, sclerostin, and osteoprotegerin regulating bone formation and bone loss (Hughes et al., 2010; Nakashima et al., 2011; Xiong et al., 2011). Increased numbers and/or over-activation of and other defects in osteoclasts can lead to the development of diseases characterized by a net decrease in bone mass or bone malformations. This can eventually result in low bone mass (osteopenia) or osteoporosis. The most common of such diseases, and perhaps the best known, is osteoporosis occurring particularly in women after the onset of menopause. In fact, osteoporosis is the most significant underlying cause of skeletal fractures in late middle-aged and elderly women. While estrogen deficiency has been strongly implicated as a factor in postmenopausal osteoporosis, there is longstanding evidence that remodeling is a locally controlled process that takes place in discrete packets throughout the skeleton. Further diseases associated with bone loss include Paget's disease, periodontal disease, osteosarcoma cancer, bone metastasis and inflammation-associated bone loss like in the context of rheumatoid arthritis, psoriatic arthritis, spondyloarthritis, SLE and systemic sclerosis.

Patients with a decreased bone mass are at a higher risk of invalidity due to fractures and given the rapidly aging population, medical costs have become a serious problem. Currently used therapeutics specifically targeting bone loss, e.g., in the osteoporosis space include bisphosphonates, calcitonin, SERMs, and anti-RANKL antibodies. The gold standard therapy bisphosphonates is taken up by osteoclasts and induces apoptosis; however, one of the pitfalls of biphosphonates include contraindications in case of kidney failure, a common problem in the aging population (e.g., target population of osteoporosis treatment) and the extremely long uptake in bone, which has inherent safety risks. Calcitonin, a natural ligand for its receptor on osteoclasts, inhibits osteoclast function but is, however, second-line choice in patients with long-term corticosteroid therapy. Biological agents like anti-RANKL antibodies are preferred for their high target specificity (WO2012/163887; WO2008/142164).

The development of anti-osteoclastogenic therapeutics is often based on the existing molecules described above by linking them or producing them as small molecules. Other upcoming therapeutics are either chemical-based, natural product-based or biological-based, which render them the qualities of greater cost-effectiveness, safety and target specificity, respectively (Kim et al., 2013). While most of them inhibit osteoclast formation from osteoclast precursors (OCP) to mononuclear osteoclasts (mOC), hence, further influencing fusion and function, therapeutics specifically inhibiting the fusion into multinucleated osteoclasts and, in particular, targeting the fusogenic molecules, are lacking.

Dendritic cell-specific transmembrane protein (DC-STAMP) is essential for cell-cell fusion in osteoclasts (Yagi et al., 2005) and in vitro addition of an antibody blocks formation of multinucleated osteoclasts (WO2010/127180). Although the mechanism is poorly understood, DC-STAMP and its putative ligand might induce some fusogenic molecules as DC-STAMP is shown to have signaling properties. As its expression in dendritic cells (DC) influences differentiation by suppressing granulocyte development, but also phagocytosis to reduce antigen-presenting capability of DCs (Zhang et al., 2014), one must be aware of possible side effects by blocking DC-STAMP.

Desialylation was also shown to block the fusion from TRAP-positive mononuclear cells into multinuclear osteoclasts indicating the essential role of sialic acids. Both alpha (2,6)-linked sialic acid and alpha (2,3)-linked sialic acid are demonstrated on osteoclast precursors and during osteoclast differentiation, but only the alpha (2,6)-linked sialic acid was suggested to have a role in fusion (Takahata et al., 2007).

Although alpha (2,6)-linked sialic acid is a possible ligand for siglec-15, the same group does not particularly put this binding forward in the explanation for the osteoclastogenic properties of siglec-15 (Kameda et al., 2013). They and others (Hiruma et al., 2011; Ishida-Kitagawa et al., 2012; Hiruma et al., 2013) describe the association of siglec-15 with DNAX-activating protein 12 kDa (DAP12), making use of its immunoreceptor tyrosine-based activation motif (ITAM-motif) to co-stimulate the RANK-RANKL pathway. Disruption of this stimulation via siglec-15 in vitro or ex vivo through deficiency or blockage interferes with the development of functional multinucleated osteoclasts (WO2012/045481; M. Stuible et al., 2014). Siglec-15-deficient mice were also shown to be mildly osteopetrotic.

Xiao et al., 2012, explored osteoporosis gene expression profiles in monocytes using a high-throughput microarray platform by grouping individual differentially expressed genes into gene sets and gene ontology terms. A group of 49 genes were assigned in nine clusters using a graph clustering method, including siglec-1 in cluster 1, of which the genes were enriched in similar pathways of immune responses and circulatory system processes. However, Takahata et al., 2007, have appointed a possible sialoadhesin ligand alpha (2,3)-linked sialic acid to only have a minor contribution in fusion of osteoclasts and moreover observed a decreased expression of sialoadhesin with osteoclast differentiation. This led to the assumption that siglec-15, a siglec with a different expression pattern and strikingly different structure and signaling capacity than siglec-1, is the only siglec that is upregulated during osteoclastogenesis (Hiruma et al., 2011; Kameda et al., 2013).

BRIEF SUMMARY

It was, therefore, unexpectedly shown in this disclosure that sialoadhesin is actually extensively upregulated during osteoclast development and that sialoadhesin has a functional role in the formation of multinucleated osteoclasts.

Methods to deliver a cargo moiety to a sialoadhesin-expressing cell has been described in, e.g., WO2008/093166 but is limited to the use of conjugates and is aimed to provoke, modulate or eradicate an immune response.

This disclosure focuses on sialoadhesin as a target in order to treat metabolic and genetic bone-disease.

The disclosure provides compositions and methods for modulating osteoclast formation, survival and function. In one aspect, the disclosure provides compositions and methods for inhibiting osteoclastogenesis and/or decreasing osteoclast activity in a cell population comprising at least one osteoclast and/or osteoclast precursor cell. The methods involve providing an Sn-binding moiety, in particular, an antibody specifically binding Sn, whereby contact with the Sn-binding moiety decreases osteoclast activity, survival and/or function. The disclosure further relates to a method for the prevention and/or treatment of at least one bone disease and/or disorder, the method comprising administering, to a subject in need thereof, a pharmaceutically active amount of an Sn-binding moiety, and/or a pharmaceutical composition comprising the same. More in particular, the disclosure relates to a sialoadhesin binding moiety for use in treating bone diseases and/or disorders, especially metabolic and genetic bone-disease associated with aberrant osteoclast activity, and characterized by a decrease in bone mass or bone malformations. In a preferred embodiment, the Sn-binding moiety is an antibody, in particular, a monoclonal antibody or a functional fragment thereof.

BRIEF DESCRIPTION OF THE DRAWINGS

FIG. 1A: Detection of cathepsin K, sialoadhesin, CD68 and cell nuclei (DAPI) on knee synovial tissue of a patient with Rheumatoid Arthritis by immunofluorescence indicates co-localization of Sn on osteoclast precursor cells. Scale bar represents 75 µm. FIG. 1B: CD14$^+$ PBMCs of a healthy volunteer were stimulated with M-CSF and RANKL in the presence of either 0.5 µg/ml monoclonal anti-human Sn antibody (mAb) 7D2 or its isotype control mouse IgG1. TRAP-positive mononuclear, multinuclear and fusing osteoclasts were counted of three replicates per condition. Error bars represent standard error of the mean. Student's t-test was applied to determine significant differences with * indicating $p<0.05$.

FIG. 3B: RNA expression of sialoadhesin in wild-type mice.

FIG. 4A: Histological scores of knees from wild-type (n=9) and sialoadhesin knockout mice (n=7) 60 days after induction of CIA. In particular, the extent of bone erosion was different in Sn KO mice compared to wild-type mice with Mann Whitney U tests with * indicating $p<0.05$. FIG. 4B: Micro Computed Tomography slices of femur and patella showing a more irregular bone structure in the femoral condyle and epicondyle of an arthritic wild-type mouse than of an arthritic Sn knockout mouse.

FIG. 5A: CTX-1 serum levels, as a marker for bone resorption at day 9 after induction of arthritis with an anti-collagen antibody cocktail. CTX-1 levels were measured in mice with a total clinical score of ≥3. Average CTX-1 level in the Sn knockout mice (n=3) is shown in percentage as compared to the average level of CTX-1 in the group of WT mice (n=4). Error bars represent standard error of the mean. Significance of the lower level of CTX-1 in the Sn KO mice was tested with Student's t-test with * indicating $p<0.05$. FIG. 5B: Visualization of the cortical pores in the cortex of the tibia from representative mice from each group at day 14 by micro CT (on the right side, the pores are filled for visualization purpose so the WT mouse has a higher number of pores/cortical volume than the Sn KO mouse). Specifically, these mice have a cortical porosity (ratio pores volume/total cortical volume) of 0.081 for the wild-type mouse and 0.061 for the Sn knockout mouse.

FIG. 6A: Micro CT analysis and measurement of the bone parameters trabecular bone volume/total volume (BV/TV) and trabecular separation of the tibia (Tb.Sp) is shown in percentage as compared to the average value of the sham-operated WT group. n=5 for WT sham, n=6 for WT OVX, n=5 for KO sham and n=6 for KO OVX. Error bars represent standard error of the mean. Significance of the loss of trabecular volume and the gain of bone marrow cavity 6 weeks after ovariectomy as a measure for osteoporosis was tested with Student's t-test with ** indicating $p<0.01$. FIG. 6B: Representative pictures from the tibial trabecular network of mice from the group of either WT or Sn KO sham-operated or ovariectomized mice (OVX).

FIG. 7A: Bone marrow cells of wild-type mice were stimulated with M-CSF and RANKL in the presence of either 0.5 µg/ml of an in-house-produced monoclonal anti-mouse Sn antibody (mSn mAb), its isotype or commercially available anti-mouse Sn antibodies 3D6.112, its isotype and MOMA-1. TRAP-positive multinucleated cells were counted of two replicates per condition. Error bars represent standard error of the mean. FIG. 7B: Micro CT 3D-dimension rendered image of an arthritic knee from a PBS-treated mouse and a monoclonal anti-mouse Sn-treated mouse 42 days after induction with collagen. Bone erosion is more pronounced on the condyle and epicondyle of the femur of the PBS-treated mouse than of the antibody-treated mouse.

DETAILED DESCRIPTION

Figure 1A:
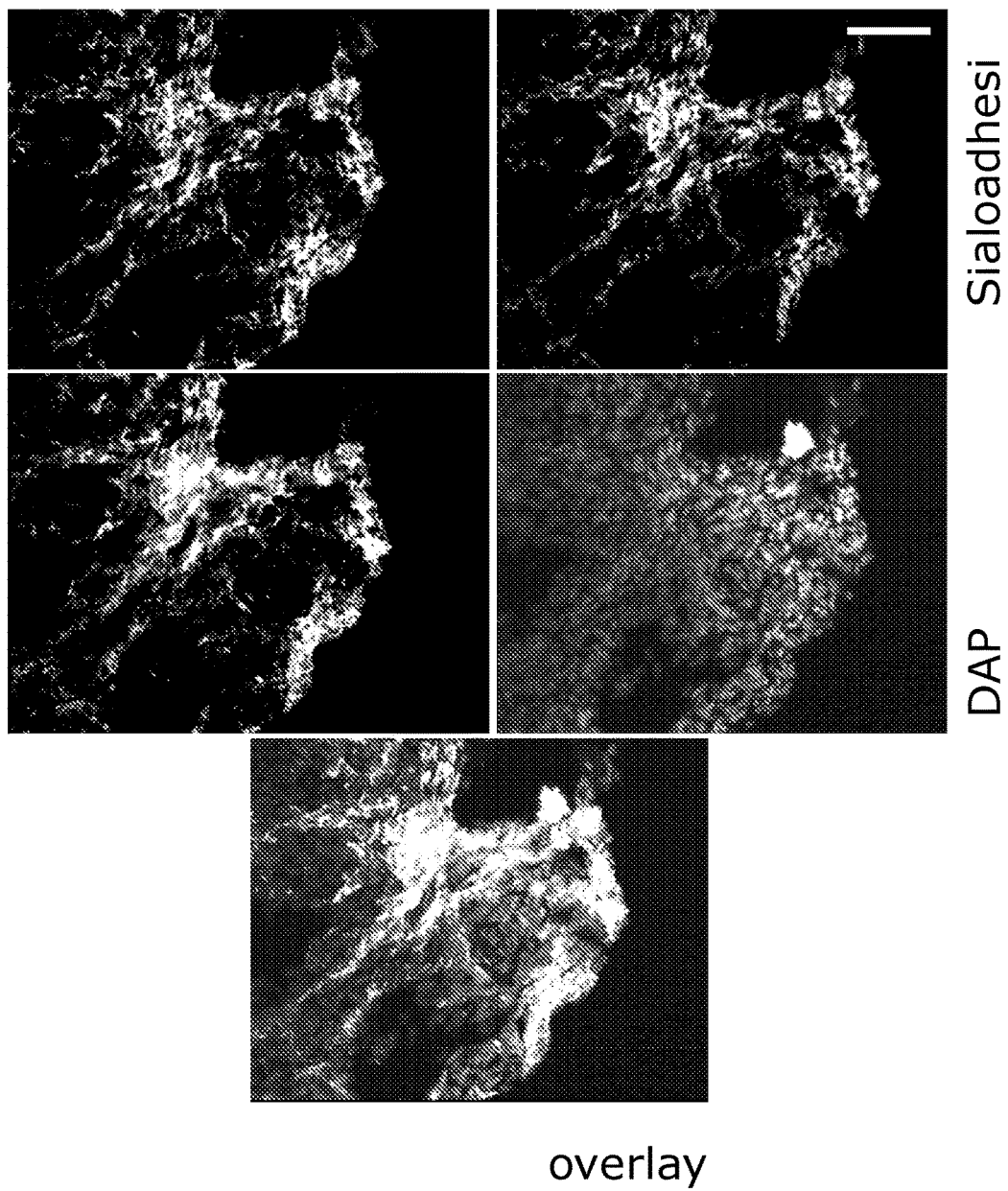
FIGS. 1A and 1B: In humans, sialoadhesin is present on osteoclast precursor cells and blocking sialoadhesin interferes with fusion of osteoclasts.

This disclosure will now be further described. In the following passages, different aspects of the disclosure are defined in more detail. Each aspect so defined may be combined with any other aspect or aspects unless clearly indicated to the contrary. As used in the specification and the appended claims, the singular forms "a," "an," and "the" include plural referents unless the context clearly dictates otherwise. By way of example, "a compound" means one compound or more than one compound. Throughout the description and claims of this specification, the word "comprise" and other forms of the word, such as "comprising" and "comprises," means "including, but not limited to," and is not intended to exclude, for example, other additives, components, integers, or steps. The terms described above and others used in the specification are well understood to those in the art. All references, and teachings specifically referred to, cited in the present specification are hereby incorporated by reference in their entirety.

This disclosure provides sialoadhesin (Sn) as a therapeutic target in bone diseases, in particular, diseases or disorders associated with a decreased bone mineral density.

It has been demonstrated for the first time in the current disclosure that sialoadhesin (Sn) promotes differentiation of osteoclasts and that osteoclasts and osteoclast precursors express sialoadhesin. It was further proven that sialoadhesin has a functional role in the formation of multinucleated osteoclasts. Moreover, it was shown that sialoadhesin-deficient mice are more resistant to inflammation-induced bone erosion during collagen-induced arthritis.

As such, sialoadhesin ligands find use in preventing differentiation of osteoclasts, in particular, in preventing or reducing aberrant osteoclast activity, osteoclast fusion and/or survival, and more in particular, in the treatment and/or prevention of bone loss.

In one aspect, the disclosure describes compounds and methods for the treatment of bone disease. The term "bone disease" refers to a medical condition that affects the bone. In particular, the bone disease is characterized by an aberrant osteoclast activity resulting in bone loss and/or bone malformation. "Bone loss disorders" or "bone loss-associated disorders" include conditions and diseases that are characterized by a net decrease in bone mass and/or bone malformations, and wherein the inhibition of bone loss is desirable. Among such conditions and disorders are osteoporosis, osteomyelitis, (Juvenile) Paget's disease, periodontitis, hypercalcemia, osteonecrosis, osteosarcoma, osteolytic metastases, familial expansile osteolysis, Expansile skeletal and idiopathic hyper phosphatasia, hyperostosis corticalis deformans juvenilis, Camurati Engelmann disease, prosthetic loosening, periprostetic osteolysis, cleiodocranial dysplasia (CCD), multiple myeloma, bone loss due to immobilization and bone loss associated with a disease selected from the group consisting of cachexia, anorexia, alopecia, and inflammatory diseases selected from the group consisting of rheumatoid arthritis, psoriatic arthritis, psoriasis, spondyloarthritis, SLE, systemic sclerosis and inflammatory bowel disease. The "bone mineral density" (BMD; or bone density) is a medical term normally referring to the amount of mineral matter per square centimeter of bones. It is most frequently measured by X-ray absorptiometry or tomography. Reference to an "aberrant osteoclast activity" should be understood as a reference to an excessive, impaired or dysfunctional osteoclast activity in relation to a physiologically normal osteoclast activity.

The methods involve administering an Sn binding moiety to a patient having a bone disease. Also provided are methods for decreasing osteoclast activity and/or decreasing osteoclast-mediated bone resorption in a patient using an Sn binding moiety. In a preferred embodiment, the disclosure provides methods for treating a variety of osteoporosis disorders, such as primary osteoporosis, endocrine osteoporosis (hyperthyroidism, hyperparathyroidism, Cushing's syndrome, and acromegaly), post-menopausal osteoporosis, hereditary and congenital forms of osteoporosis (osteogenesis imperfecta, homocystinuria, Menkes' syndrome, and Rile-Day syndrome) and osteoporosis due to immobilization of extremities, glucocorticoid-induced osteoporosis, and immunosuppressant (post-transplant) osteoporosis. Also provided are methods for decreasing osteoclast activity in patients having an osteoporosis disorder. The methods involve administering an Sn binding moiety as described herein to a patient having an osteoporosis disorder, in particular, post-menopausal osteoporosis.

In another preferred embodiment, the disclosure provides methods for treating bone loss due to or resulting from disease, in particular, bone cancer or bone metastases (osteolytic metastasis), or due to hormonal therapy or chemotherapy in the treatment of cancer, in particular, breast or prostate cancer.

As demonstrated herein, the Sn binding moieties of this disclosure decrease the osteoclast activity. Sn binding moieties are able to decrease osteoclast differentiation and bone resorption, including osteoclast differentiation and bone resorption promoted by a variety of agents. By "osteoclast differentiation" is meant the formation of a cell having osteoclast activity from a cell that lacks the activity but is of the osteoclast lineage, and is, therefore, referred to as an "osteoclast precursor." Bone remodeling involves regulation by osteocytes of the synthesis of bone matrix by osteoblasts and its resorption by osteoclast cells. Osteoclasts derived from hematopoietic cells are unique forms of tissue macrophages that have the capacity to resorb bone tissue. Osteoblasts are specialized fibroblasts that have the capacity of secreting bone collagen. Osteocytes represent 90% of the bone cells and control osteoblast and osteoclast formation and function. The term "osteoclast precursor" includes cells that give rise to osteoclasts without proliferation, as well as cells that go through one or more rounds of cell division to provide cells that give rise to osteoclasts without proliferation. Osteoclast precursor cells (OCP) include bone marrow-derived macrophages, "inflammatory" blood monocytes, $CD14^+$ $CD11b^+$ cells in the spleen and cathepsin K-positive macrophages in synovial tissue.

"Osteoclast activity" includes, but is not limited to, the ability to mobilize or break down bone or dentate mineral. Activities also include secretion of enzymes that modify signaling in the bone (MMP-9) and secretion of cytokines including nitric oxide, IL-1, TNFalpha, and TL-6 that further modify osteoblastic activity or bone survival in general. By "decreasing osteoclast activity" is meant decreasing, partially or completely, one or more osteoclast activities, such as resorption, release of proteolytic enzymes, acid secretion and adhesion. "Decreasing osteoclast activity" also includes reducing osteoclast differentiation (i.e., reducing osteoclastogenesis), whereby a precursor cell is kept from differentiating and obtaining the ability to exert an osteoclast activity. In a particular embodiment, the Sn binding moiety is capable of preventing or reducing osteoclast fusion.

By "reducing osteoclastogenesis" is meant a down-regulation of osteoclast differentiation from osteoclast precursors of at least about 10%, 20%, 30%, 40%, 50%, 60%, 70%, 80%, 90% or up to 100% compared to the level of osteoclastogenesis observed in absence of intervention as described herein, in particular, a down-regulation of osteoclast differentiation of at least 40%, even more in particular, of at least 50% or 60%.

In a further aspect, the disclosure provides compositions and methods for decreasing osteoclast activity in a cell population comprising at least one osteoclast or osteoclast precursor cell. The methods involve contacting the osteoclast or osteoclast precursor cell with an Sn binding moiety, whereby contact with an Sn binding moiety decreases osteoclast activity. Cell populations may be in vivo or in vitro populations. Preferred cell populations are in vivo cell populations that include osteoclasts and/or (bone marrow-derived) precursor cells.

A "sialoadhesin (Sn) binding moiety" or "ligand" binds specifically to sialoadhesin (CD169; Siglec-1). The term "binds specifically" as used herein is intended to indicate that a sialoadhesin binding moiety interacts preferentially with sialoadhesin and does not significantly interact with other proteins or other molecules. Examples of such other molecules include Siglec-15 (Sialic-acid binding immunoglobulin-like lectin 15; CD33 antigen-like 3). In particular, a sialoadhesin binding moiety binds to an extracellular portion of sialoadhesin expressed by a cell. Further, a sialoadhesin binding moiety binds specifically with sialoadhesin present in the cell membrane of a target cell.

Sn binding moieties of the disclosure can include a variety of different types of molecules including those that specifically bind sialoadhesin, and/or antagonize (the function of) the sialoadhesin receptor. Such Sn binding moieties include small molecules, polypeptides or nucleic acids (aptamers), antibodies and the like. In one embodiment of the disclosure, the moiety is non-conjugated, i.e., not directly coupled or linked to another molecule or compound. In a further embodiment, the Sn binding moiety is not a natural sialylated ligand for sialoadhesin such as CD43, galactose-type C-type lectin 1, and the MUC1 antigen.

Suitable Sn binding moieties for use in the compositions and methods provided herein have a variety of characteristics, and may be identified in a number of ways. Sn binding moieties capable of treating bone disease may be identified by their ability to inhibit osteoclastogenesis and/or osteoclast activity. For example, putative Sn binding moieties may be screened by incubation with osteoclast precursor cells under conditions known to promote osteoclast differentiation, as demonstrated in the present examples. The method comprises incubating an osteoclast precursor for a time and under conditions suitable for differentiation in the absence and presence of a putative Sn binding moiety, and measuring the formation of mature osteoclasts, wherein a decrease in the number of mature osteoclasts in the presence of the putative agent is indicative of the identification of an Sn binding moiety capable of inhibiting osteoclast activation or survival. Conditions include, e.g., the presence of RANK-L and M-CSF. Formation of osteoclasts may be detected, e.g., by measuring TRAP activity as described herein. For example, the method may include using bone marrow cells that can be incubated with compounds in the presence of RANK-L and M-CSF. Other assays include monitoring characteristic osteoclastic proteins including calcitonin receptor, cathepsin K and tartrate-resistant acid phosphatase (TRAP) (as described herein). All of these are highly specific for osteoclasts.

Sn binding moieties capable of treating bone disease as described herein may also be identified by their ability to modulate bone resorption in vivo by methods as known in the art. For example, bone resorption in vivo and its modulation is assessed by examining effects of compounds in rodents (mice and rats) following ovariectomy or orchiectomy, PTH treatment or immobilization. Six weeks after ovariectomy or orchiectomy, there is bone loss up to 10%, which should be reversed by the administration of an osteoclast inhibitory agent, such as an Sn binding moiety as described herein. Bone loss is quantitated histomorphometrically or by bone mineral density measurements (Pixi-mus) or by microCT examination of 3-D structural elements. These are well-known straightforward techniques.

In one embodiment, the sialoadhesin binding moiety is an antibody. The term "antibody" refers to polyclonal antibodies, monoclonal antibodies (mAbs), chimeric antibodies, and humanized antibodies. The disclosure further encompasses antigen binding antibody fragments and molecules having antigen binding functionality.

The term "antibody" generally refers to an intact immunoglobulin having four polypeptide chains, two heavy (H) chains and two light (L) chains linked by disulfide bonds. The term "antibody fragment" as used herein refers to sialoadhesin binding antibody fragments illustratively including, but not limited to, a Fab fragment, a Fab' fragment, a F(ab')2 fragment, an Fd fragment, an Fv fragment, an scFv fragment, a domain antibody (dAb), heavy chain antibodies (hcAb), minibodies (Tramontano et al., 1994), a variable domain of camelid heavy chain antibody (VHH), a variable domain of the new antigen receptor (VNAR) and engineered CH2 domains (nanoantibodies; Dimitrov, 2009). It further includes peptides and scaffolds with antibody-like characteristics, such as single chain antiparallel coiled protein (alphabodies; WO2010/066740).

An anti-sialoadhesin antibody and/or sialoadhesin binding antibody fragment of this disclosure is capable of specifically binding sialoadhesin. A preferred sialoadhesin binding moiety binds sialoadhesin with greater affinity than it binds another member of the Siglec family, especially Siglec-15.

A preferred sialoadhesin binding moiety is characterized by specific binding activity for sialoadhesin of at least about $1\times10^5$ $M^{-1}$. In further embodiments, a preferred sialoadhesin binding moiety has a specific binding affinity for sialoadhesin of at least about $1\times10^6$ $M^{-1}$. In still further embodiments, a preferred sialoadhesin binding moiety has a specific binding affinity for sialoadhesin of at least about $1\times10^7 M^{-1}$.

Anti-sialoadhesin antibodies and sialoadhesin binding antibody fragments may be provided by any method, illustratively including, but not limited to, immunization, isolation and purification, enzymatic cleavage of an intact immunoglobulin, screening of phage display libraries, chemical synthesis of a desired sialoadhesin binding peptide or protein, and production by recombinant nucleic acid technology. Combinations of such methods may also be used.

An anti-sialoadhesin antibody can be made by immunization using as an antigen a full-length sialoadhesin or a peptide fragment of sialoadhesin. Such proteins and peptides may be, illustratively, a human, pig, sheep, rat, mouse, monkey, ape, or other sialoadhesin protein or peptide. Exemplary human, porcine and mouse sialoadhesin protein and nucleic acid sequences included herein are, respectively, identified by GenBank Accession number NM 023068 GI:89142743 (human); GenBank Accession number AF509585.1 GI:31323698 (porcine); and GenBank Accession number NM_011426 GI:226958331 (mouse). In a specific aspect of the disclosure, the antibody is non-conjugated, i.e., not directly coupled or linked to another molecule or compound.

Extracellular portions of sialoadhesin from various species have been characterized, as having sialic acid binding sites, as exemplified in D. Nath et al., 1995; M. Vinson et al., 1996; A. Hartnell et al., 2001; and N. Vanderheijden et al., 2003. For example, an extracellular portion of human sialoadhesin extends from amino acid 1-1642, an extracellular portion of porcine sialoadhesin extends from amino acid 1-1643 and an extracellular portion of mouse sialoadhesin extends from amino acid 1-1638, each with reference to the sequences described herein. A sialoadhesin fragment used as an antigen in preparation of a sialoadhesin binding antibody preferably includes one or more Ig-like domains. In a particular embodiment, the sialoadhesin binding moiety of this disclosure specifically binds the extracellular portion of human sialoadhesin, i.e., the portion extending from amino acid 1 up to amino acid 1642.

Antigens may be prepared by any of various methods, including isolation from natural sources, recombinant production or by chemical synthetic techniques. Sialoadhesin proteins and peptides for use as antigens in preparation of a sialoadhesin binding antibody are similarly prepared by any of various techniques. A peptide portion of sialoadhesin or other antigen may be made more immunogenic if desired by linkage to a carrier molecule such as bovine serum albumin or keyhole limpet hemocyanin. Such a linkage may be accomplished by any of various techniques, illustratively including, but not limited to, conjugation and expression of a fusion protein.

Recombinantly expressed proteins and peptides, such as, but not limited to, sialoadhesin and sialoadhesin fragments, may be tagged to allow for easier isolation. For instance, such proteins and peptides may be Fc-tagged.

Antibodies, antigen binding fragments and methods for their generation are known in the art and such antibodies, antigen binding fragments and methods are described in further detail, for instance, in *Antibody Engineering*, R. Kontermann and S. Dubel (eds), Springer, 2001; E. Harlow and D. Lane, *Antibodies: A Laboratory Manual*, Cold Spring Harbor Laboratory Press, 1988, F. Ausubel et al. (eds.).

The term "antigen" in the context of making a sialoadhesin binding moiety refers to sialoadhesin as described herein or an antigenic portion thereof. In a particular embodiment, an antigenic portion of sialoadhesin includes a portion of sialoadhesin present external to a cell expressing sialoadhesin.

An antibody that is a sialoadhesin binding moiety may be made using a native sialoadhesin, such as exemplified by amino acid sequences included herein, and/or peptide fragments thereof, as an antigen. An antibody that is a sialoadhesin binding moiety may also be made using a sialoadhesin homologue, modified sialoadhesin and/or fragment thereof as an antigen.

A specific example of a sialoadhesin binding moiety is a mouse monoclonal antibody 7D2 (mAb 7D2) which binds human sialoadhesin. MAb 7D2 was raised against an Fc fusion protein containing the N-terminal four domains of human sialoadhesin. MAb 7D2 is further described in A. Hartnell et al., 2001, and is commercially available. Another example is mouse monoclonal clone 7-239 (mAb 7-239), which binds human sialoadhesin. mAb 7-239 was raised again human rhinovirus-treated dendritic cells and is commercially available.

As noted above, sialoadhesin is a sialic acid-binding immunoglobulin-like lectin. Sialoadhesin binds sialic acid with a superior affinity toward α2-3 sialic acid residues compared to α2-6 and α2-8 sialic acid residues. Bound sialic acid residues illustratively include Siaα2-3Galβ1-3GalNAc; Siaα2-3Galβ1-3GlcNAc; and Siaα2-3Galβ1-4GlcNAc, Siaα2-6Galβ1-3GalNAc and Siaα2-8Neu5Acα2-3Galβ1-3GalNAc. In a further embodiment of this disclosure, a sialoadhesin binding moiety includes a sialoadhesin ligand, preferably a sialylated organic structure such as, but not limited to, a sialylated protein or peptide, lipid, and/or carbohydrate, and/or a sialyl-like synthetic carbohydrate.

It is understood that a sialoadhesin binding moiety as described herein may be used alone or in conjunction with other factors for the treatment of bone disorders. In one embodiment, an Sn binding moiety is used in combination with other osteoclast inhibitors, or agents that find use in treating bone disorders as described herein. Several agents that are approved for treating bone disorders include estrogen replacement therapies, including estrogens, selective estrogen receptor modulators (raloxifene (EVISTA®)), two bisphosphonates, alendronate and risedronate, calcitonin and parathyroid hormone, including Teriparatide (PTH (1034) (brand name FORTEO®), and additional agents, such as RANKL inhibitors (e.g., denosumab), cathepsin K inhibitors, integrin inhibitors, src inhibitors, and V-ATPase inhibitors, including bafilomycin; also, additional bisphosphonates (zoledronic acid, clodronate, tiludronate, pamidronate, etidronate, ibandronate) and partial estrogen agonists and antagonists including genistein, daidzein and related phytoestrogens and tamoxifen; and bone binding transition metals gallium, thallium, and indium, and inhibitors of chloride channel activity.

In a further embodiment, this disclosure relates to a pharmaceutical composition, comprising or consisting of a sialoadhesin binding moiety, especially an antibody or functional fragment thereof, and a pharmaceutically acceptable carrier, excipient and/or additive as known in the art. Preferably, the Sn binding moiety or antibody is non-conjugated, i.e., not coupled or linked to other molecules. The composition of the disclosure is suitable for administration directly to the subject to be treated. Formulations typically comprise at least one active ingredient (e.g., the anti-Sn antibody), as defined above, together with one or more acceptable carriers. Each carrier should be both pharmaceutically and physiologically acceptable in the sense of being compatible with the other ingredients and not injurious to the patient. Optionally, the composition of the disclosure further comprises a buffering agent. Supplementary active ingredients can also be incorporated into the composition.

As used herein, "pharmaceutically acceptable carrier" comprises any of standard pharmaceutically accepted carriers known to those of ordinary skill in the art in formulating pharmaceutical compositions. Thus, the ligand or moiety of the disclosure may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or the like, or as solid formulations in appropriate excipients. Additionally, the formulations may include bactericidal agents, stabilizers, buffers, emulsifiers, preservatives, sweetening agents, lubricants, or the like. Suitable formulations may be found in, among others, *Remington's Pharmaceutical Sciences,* 17th edition, Mack Publishing Co., Philadelphia, Pa., 1985, and *Handbook of Pharmaceutical Excipients,* 3rd Ed, A. H. Kibbe, ed., Washington D.C., American Pharmaceutical Association, 2000; both of which are hereby incorporated by reference herein in their entirety. The pharmaceutical compositions described herein can be made in a manner well known to those skilled in the art.

It will be appreciated that different means of application are preferred for the different intended uses of the Sn binding moieties disclosed herein. Further, some intended uses may be achieved by more than one means of application. For example, systemic application might be preferred for the treatment of osteoporosis, bone loss due to bone cancer or bone metastases, and bone loss associated with inflammatory disease.

The concentrations of the Sn binding moieties will be determined empirically in accordance with conventional procedures for the particular purpose. Generally, for administering the moieties in vivo for therapeutic purposes, the subject formulations are given at a pharmacologically effective dose. By "pharmacologically effective amount" or "pharmacologically effective dose" is meant an amount sufficient to produce the desired physiological effect or amount capable of achieving the desired result, particularly for treating the disorder or disease condition, including reducing or eliminating one or more symptoms of the disorder or disease.

The amount administered to the subject will vary depending upon what is being administered, the purpose of the administration, such as prophylaxis or therapy, the state of the host, the manner of administration, the number of administrations, interval between administrations, and the like. These can be determined empirically by those skilled in the art and may be adjusted for the extent of the therapeutic response. Factors to consider in determining an appropriate dose include, but are not limited to, size and weight of the subject, the age and sex of the subject, the severity of the symptom, the stage of the disease, method of delivery of the agent, half-life of the agents, and efficacy of the agents. Stage of the disease to consider includes whether the disease is acute or chronic, in the relapsing or remitting phase, and the progressiveness of the disease. Determining the dosages and times of administration for a therapeutically effective amount are well within the skill of the ordinary person in the art.

The toxicity and therapeutic efficacy are generally determined by cell culture assays and/or experimental animals, typically by determining an LD50 (lethal dose to 50% of the test population) and ED50 (therapeutic effectiveness in 50% of the test population). The dose ratio of toxicity and therapeutic effectiveness is the therapeutic index. Preferred are compositions, individually or in combination, exhibiting high therapeutic indices. Determination of the effective amount is well within the skill of those in the art.

The term "preventing and/or treating" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or duration of the disease and/or the symptoms associated therewith and/or preventing a further increase in the severity of the disease and/or of any symptoms associated therewith.

The different aspects of this disclosure are illustrated by, but not limited to, the examples detailed hereafter.

EXAMPLES

Materials and Methods
Patients

Synovial membrane biopsies were obtained by needle arthroscopy of patients with rheumatoid arthritis.
In-House Anti-Sn Antibody Production Monoclonal Abs were generated in rat by immunization with the soluble extracellular part (AA 20-1339) of mSn (Synaptic Systems, Germany). Lymph nodes were isolated and fused with myeloma cells to generate a hybridoma cell line. Clones were tested for their ability to bind the soluble mSn and mSn expressed on CHO cells and subsequently subcloned twice to guarantee their monoclonal nature.

The hybridoma for the isotype control was purchased at ATCC, USA, and treated similar to the rat anti-mSn Ab. Hybridomas were grown to confluency in DMEM 10% IgG depleted FCS, 1% P/S and medium was harvested up to six times. The Ab was purified from the medium on a protein G column to a purity of >95%, protein-containing fractions were pooled and dialyzed to PBS with endotoxin levels <1 EU/ml.
Osteoclast Formation Assay Mouse bone marrow cells were flushed from femurs and tibiae of wild-type or Sn knockout mice. After red blood cell lysis, $1.5 \times 10^5$ cells were seeded in 96-well plates in α-MEM (Life Technologies) medium containing 20 ng/ml recombinant macrophage colony-stimulating factor (M-CSF; Sigma-Aldrich) and 50 ng/ml recombinant Receptor activator of nuclear factor kappa-β ligand (RANKL; Sigma-Aldrich) (alternatively, 24-well plates on glass coverslips for immunofluorescence staining can be used). When appropriate, antibodies were added to the cells with every refreshment of the stimulation medium every three days. Anti-mouse Sn monoclonal antibodies clone 3D6.112 (AbdSerotec), the in-house antibody (obtained as described earlier) and their control isotypes were added at a concentration of 0.5 µg/ml, MOMA-1 (AbdSerotec) supernatant was diluted 1/6. TRAP activity staining was performed on day 11.

Human peripheral blood mononuclear cells (PBMCs) or synovial fluid mononuclear cells (SFMCs) were isolated from blood of healthy donors or from knee synovial fluid from a patient with Psoriatic Arthritis using a ficoll gradient (Sigma-Aldrich). After magnetic isolation of $CD14^+$ cells with CD14 MACS Microbeads (Miltenyi Biotec), $1.5 \times 10^5$ cells were seeded in a 6-well plate in α-MEM (Life Technologies) medium containing 20 ng/ml human M-CSF (R&D Systems) until 90% confluency to proliferate. $2 \times 10^4$ cells were then seeded in a 96-well plate in α-MEM (Life Technologies) medium containing 20 ng/ml human M-CSF and 2 ng/ml murine RANKL (alternatively, 24-well plates on glass coverslips for immunofluorescence staining can be used). Anti-human Sn antibodies were added to the cells with every refreshment of the stimulation medium every three days. Antibodies included clone 7D2 (Santa Cruz) and its isotype control mouse IgG1 at a concentration of 0.5 µg/ml. TRAP activity staining was performed on day 9.

TRAP activity staining was performed using a leukocyte acid phosphatase kit (Sigma-Aldrich) according to the manufacturer's instructions. Osteoclasts were identified based on their shape, nuclei ≥3 and TRAP staining. Their number was counted in 7 representative pictures per 96 wells in duplicate or triplicate per condition.
RNA Isolation, cDNA Synthesis and qPCR Analysis RNA was extracted from the mouse bone marrow cell cultures at several time points (day 0 to 11) using 350 µl RLT buffer (Qiagen) following RNEASY® mini kit (Qiagen), according to the manufacturer's instructions. Genomic DNA removal and cDNA synthesis was performed using the QUANTITECT® reverse transcriptase kit (Qiagen) according to the manufacturer's instructions. qPCR analysis was performed using the LIGHTCYCLER® 480 Real-Time PCR system (Roche) and analyzed using the ΔΔCt method. 3 µl cDNA and 5 µl mixture of SENSIMIX® No-ROX kit (Bioline), primer and water were used for each reaction. Reactions were performed in duplicate. QUANTITECT® primer assays were used (Cathepsin K: QT00150730, Calcitonin receptor: QT00108864, Sialoadhesin: QT00100177, TRAP:

QT00131012). All primer sets were validated for specificity, by melting curve analysis, and efficiency, by analysis of elution series.

Immunofluoresence on Human Synovial Tissue, Human and Mouse Osteoclast Culture

IF was performed on frozen sections of synovial biopts of RA patients after fixation in aceton. The primary mouse anti-human Sn antibody (clone 7D2; Santa Cruz), rabbit anti-cathepsin K antibody (abcam) and biotin-labeled mouse IgG2b anti-CD68 (Immunosource) were applied after blocking with 2% serum (species $2^{nd}$ antibody) and 5% BSA in PBS. Primary antibodies were detected by ALEXA FLUOR®-488-labeled anti-mouse IgG1 (Life Technologies), Cy3-labeled anti-rabbit (Jackson Immuno Research) and streptavidin-ALEXA FLUOR®-647 (Life Technologies), respectively.

Slides were mounted with prolong anti-fade mounting medium with DAPI (Invitrogen). Negative control stainings were performed by using isotype controls or omission of one primary antibody. Co-localization was determined by fluorescent wide-field and confocal microscopy (Leica TCS LSI).

IF of human osteoclast culture at different time points was performed on aceton fixed glass coverslips by combining anti-human Sn antibody with ALEXA FLUOR®-555 Phalloidin (Life Technologies). Subsequently, ALEXA FLUOR®-488 AffiniPure F(ab')$_2$ fragment donkey anti-mouse IgG (Jackson Immuno Research) was applied to detect the primary antibody. Cells were visualized by confocal microscopy.

Mouse expression of sialoadhesin during different osteoclast stages was visualized accordingly by using anti-mouse Sn antibody (3D6.112 clone; AbD Serotec), followed by Biotin AffiniPure F(ab')$_2$ fragment donkey anti-rat IgG and ALEXA FLUOR®-488 streptavidin.

In Vivo Evaluation Using Collagen-Induced Arthritis (CIA)

Sialoadhesin knockout mice were generated as described in Oetke et al., 2006. Sn KO mice and wild-type controls with C57Bl6 background were 8 to 16 weeks old for CIA induction. Mice were immunized intradermally at the base of the tail with 200 µg of chicken type II collagen (CII) (Morwell Diagnostics GmbH, Zurich, Switzerland) (in 0.1 M acetic acid) emulsified in Incomplete Freund's Adjuvant+*mycobacterium Tuberculosis* H37RA (250 µg/mouse) (Difco, Lawrence, KS, USA). Twenty-one days later, mice were re-challenged with an injection of CII in Incomplete Freund's Adjuvant+*mycobacterium Tuberculosis* H37RA (250 µg/mouse).

Eight-week-old DBA/1 Rj (H-2q background) mice were obtained from Janvier, France. Mice were immunized intradermally at the base of the tail with 200 µg of chicken type II collagen (CII) (Morwell Diagnostics GmbH, Zurich, Switzerland) (in 0.1 M acetic acid) emulsified in Incomplete Freund's Adjuvant+*mycobacterium Tuberculosis* H37RA (150 µg/mouse) (Difco, Lawrence, Kans., USA). Twenty-one days later, mice were re-challenged with an injection of CII in Incomplete Freund's Adjuvant. Mice were treated intraperitoneally twice a week from day 14 after induction on until sacrifice. Treatments consisted of PBS as a negative control and the anti-Sn antibody (200 µg/mouse) in PBS.

From Day 21, mice were monitored for clinical symptoms of arthritis until the day of sacrifice (day 42 for DBA/1 mice, day 60 for C57Bl/6 mice). Clinical severity was graded as follows: 0=normal; 0.5=erythema and edema in only one digit; 1=erythema and mild edema of the footpad, or ankle or two to five digits; 2=erythema and moderate edema of two joints (footpad, ankle, two to five digits); 3=erythema and severe edema of the entire paw; 4=reduced swelling and deformation leading to incapacitated limb. The individual mouse arthritic score was obtained by summing the scores recorded for each limb. Clinical evaluations were performed by two investigators unaware of mouse identity and the mean of both scores was calculated.

Histological Evaluation of Severity of Bone Damage in Mice

Knees were fixed in 4% formaldehyde, decalcified and embedded in paraffin. Serial sections of the knee were stained with hematoxylin and eosin (H&E) or with saffranin O-fast green and inflammation and joint damage of the femorotibial and femoropatellar joints were investigated by scoring five parameters as follows: inflammation was scored on a scale of 0 (no inflammation) to 3 (severe inflamed joint) depending on the number of inflammatory cells in the synovial cavity (exudate) and synovial tissue (infiltrate). Exudate and inflammatory infiltrate were both assigned individual scores. Loss of proteoglycans was scored on a scale of 0 to 3, ranging from fully stained cartilage to destained cartilage or complete loss of articular cartilage. Cartilage destruction was scored on a scale of 0 to 3, ranging from the appearance of dead chondrocytes (empty lacunae) to complete loss of the articular cartilage. Loss of bone was scored on a scale of 0 to 5, ranging from no damage to complete loss of the bone structure. A composite score was calculated by summing the individual parameters. Scoring was executed blindly by three investigators and mean values were calculated.

In Vivo Evaluation Using Collagen Antibody Induced Arthritis (CAIA)

Sn KO mice and wild-type controls with C57/Bl6 background were 8 to 12 weeks old for CAIA induction. Eight-week-old DBA/1 Rj (H-2q background) mice for anti-Sn antibody treatment were obtained from Janvier, France. Mice were intravenously injected with 2.4 mg ARTHRITOMAB™ antibody cocktail for C57Bl/6 mice (MDBiosciences), and 2 mg ARTHRITOMAB™ antibody cocktail, respectively. Three days later, mice were intraperitoneally challenged with 100 µg LPS. DBA/1 mice were treated intraperitoneally twice a week from the day before antibody cocktail administration on until sacrifice on day 14. Treatments consisted of PBS as a negative control, isotype and the anti-Sn antibody (200 µg/mouse) in PBS. Mice were monitored daily for clinical symptoms of arthritis until sacrifice on day 14. Clinical severity was graded as described before for CIA. Bone degradation marker C-terminal telopeptide α1 chain of type I collagen (CTX-I) was measured by ELISA according to the manufacturer's instructions (Ratlaps; Immunodiagnostic Systems).

In Vivo Evaluation in Ovariectomized Mice

At a minimal age of 8 weeks, six female mice of both genotypes were either sham-operated or ovariectomized. Mice were analyzed 6 weeks later. Tibiae were excised for micro-CT imaging. Surgically removed ovaries were examined histologically and luteinizing hormone (LH) was measured in serum by ELISA to verify successful ovariectomy. Serum levels of RANKL and OPG are measured for detecting imbalance between bone loss and bone formation. Bone formation marker osteocalcin and bone degradation marker C-terminal telopeptide α1 chain of type I collagen (CTX-I) was measured by ELISA according to the manufacturer's instructions (Ratlaps; Immunodiagnostic Systems).

Commercially available C57Bl/6 mice (Harlan) are ovariectomized at 10 weeks of age. Three groups of eight mice are either injected with PBS, isotype or anti-Sn antibody. A fourth group is sham-operated. IP injections of 200 µg are given twice a week, from one week after surgery on until sacrifice at week 6. Analysis of osteoporosis and successful ovariectomy is performed as described above.

Micro Computed Tomography

Optimal scanner settings were selected based on the sample size and composition. The samples were scanned on HECTOR, using a directional X-ray source set at 100 kV, 1 mm Aluminum filtration, 10 Watt beam power. The detector was a Perkin-Elmer flat panel measuring 40×40 cm, with a pixel pitch of 200 µm. The magnification was set at 40 times resulting in a voxel pitch inside the sample of 5 µm. A total of 2000 projections of 1 second exposure time each were recorded. The data was then reconstructed using Octopus (Vlassenbroeck et al., 2007), a commercial software originally developed by UGCT, which uses a custom implementation of the standard FDK-algorithm for reconstruction of cone-beam CT data. Three-dimensional visualizations and calculations were made using the commercial rendering software VGStudioMAX (Volume Graphics) or Fiji.

Statistical Analysis

Differences in histological data between the different groups were assessed with the Mann-Whitney-U test. As the clinical score was lower in Sn KO mice, the difference in histology was expected in one direction allowing the use of the 1-tailed p-value. Differences in number of TRAP-positive cells, CTX-1 levels and bone parameters were analyzed with the Student's t-test by which the 2-tailed p-value was calculated. All analyses were performed using SPSS 20.0 statistical software (Chicago, Ill., USA).

Results

Sialoadhesin is Expressed on Osteoclast Precursors in Patients with Rheumatoid Arthritis and Ex Vivo Anti-Sn Treatment Decreases Human Osteoclast Formation, Particularly Osteoclast Fusion.

Knee synovial tissue from patients with rheumatoid arthritis was analyzed for its sialoadhesin, cathepsin K and CD68 expression by triple immunofluorescence. In numerous cells, sialoadhesin is co-localized with the osteoclast precursor marker combination cathepsin K and CD68 (FIG. 1A).

Figure 1B:
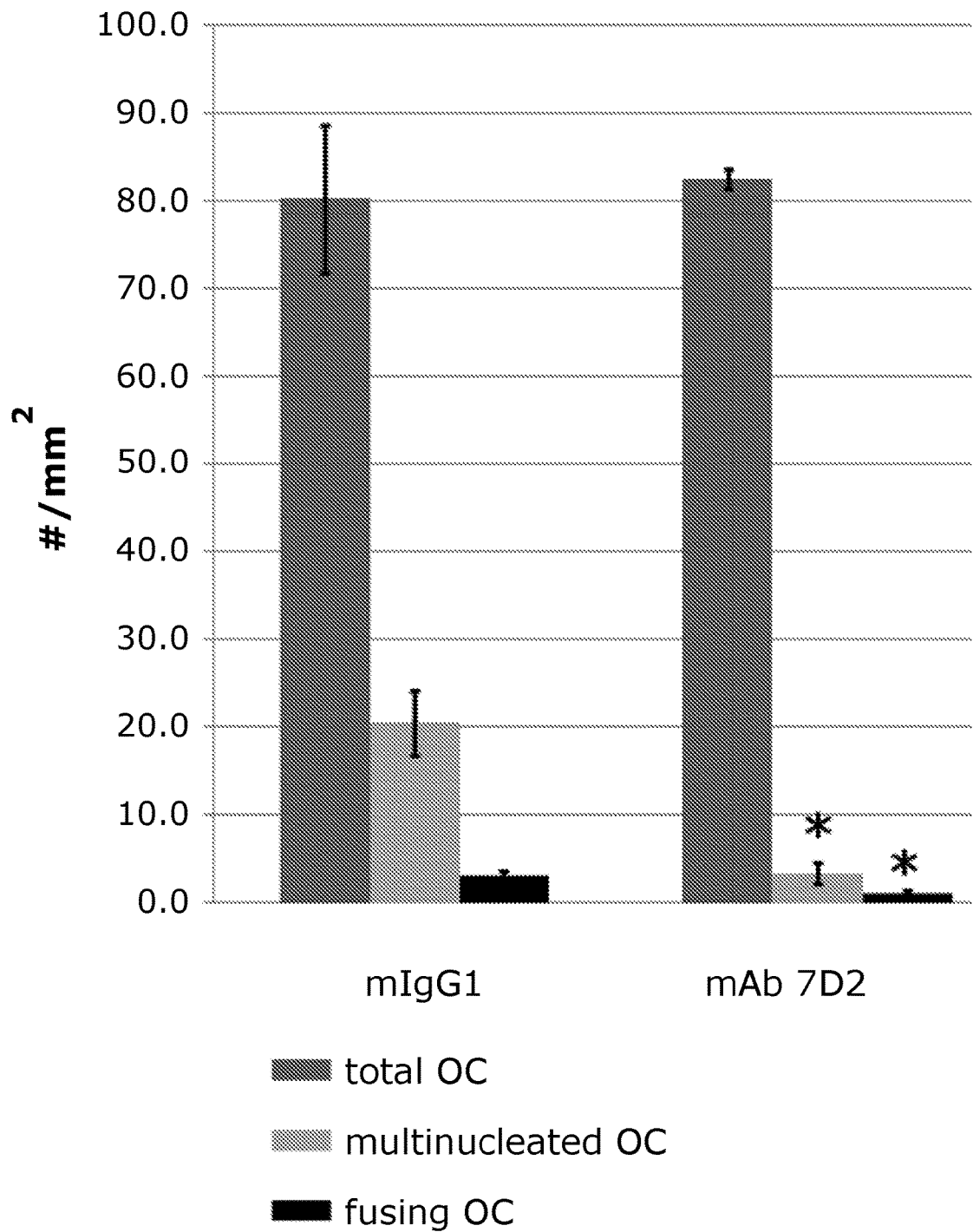

Furthermore, the addition of anti-human sialoadhesin antibody to healthy human CD14+ pheripheral blood mononuclear cells, stimulated with M-CSF and RANKL, showed a disturbed osteoclast differentiation after quantitation of TRAP-positive osteoclasts in comparison with isotype control antibody (FIG. 1B). It was remarkable that particularly ($p<0.05$) the formation of large multinucleated osteoclasts was inhibited as at least four times less large multinucleated osteoclasts were formed when incubated with an anti-human sialoadhesin antibody, suggesting a role of sialoadhesin in osteoclast fusion. Clusters of cells in which fusion was ongoing (fusing pre-osteoclasts) were three times less observed when incubated with mAb 7D2. Total osteoclasts comprising TRAP-positive mononucleated osteoclasts (or pre-osteoclasts) and fusing or fused multinucleated osteoclasts together were not significantly different.

Sialoadhesin is Specifically Expressed on Fusing Pre-Osteoclasts in Both Human and Mice.

Figure 2:
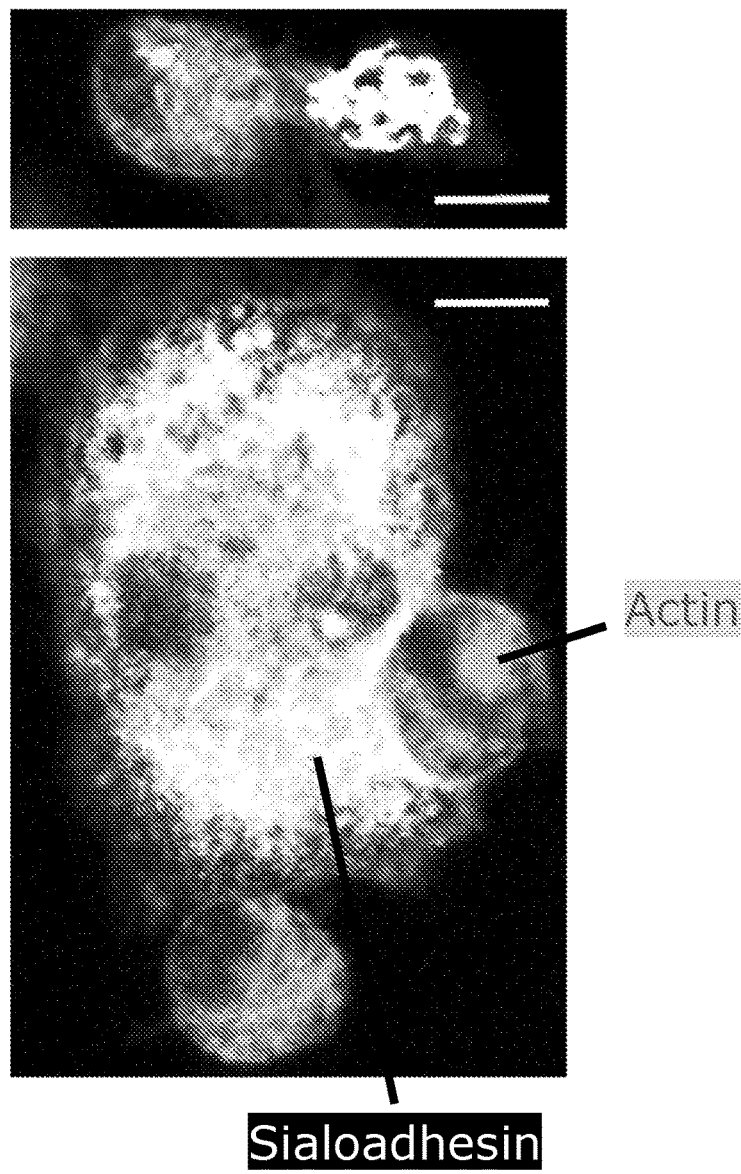
FIG. 2: Sialoadhesin is expressed on fusing pre-osteoclasts. Mouse femoral bone marrow cells were stimulated with M-CSF and RANKL. Sialoadhesin (white) was detected by immunofluorescence staining on pre-osteoclasts on different days during differentiation of the cell culture, mostly on one out of two fusing cells. Actin (grey) was used as a cell counterstain. Scale bar represents 10 µm.

Osteoclast differentiation cultures were set up from either healthy human CD14+ PBMCs, human CD14+ SFMCs from a patient with Psoriatic Arthritis or mouse bone marrow cells. Immunofluorescent detection of sialoadhesin on each type of cell culture shows its presence on one or more pre-osteoclasts in close proximity of or attached to a sialoadhesin-negative cell (FIG. 2). These results clearly suggest that stimulation with M-CSF and RANKL of these cells triggers fusion between a sialoadhesin-positive and -negative cell in the process of multinucleation of osteoclasts.

Bone Structure and Osteoclastogenesis is Disturbed in Healthy Sialoadhesin-Deficient Mice.

Knee joints of healthy wild-type and Sn knockout mice were scanned by microCT. Three-dimensional sections of the tibiae show a denser trabecular structure in the sialoadhesin-deficient mice than in wild-type mice.

Figure 3A:
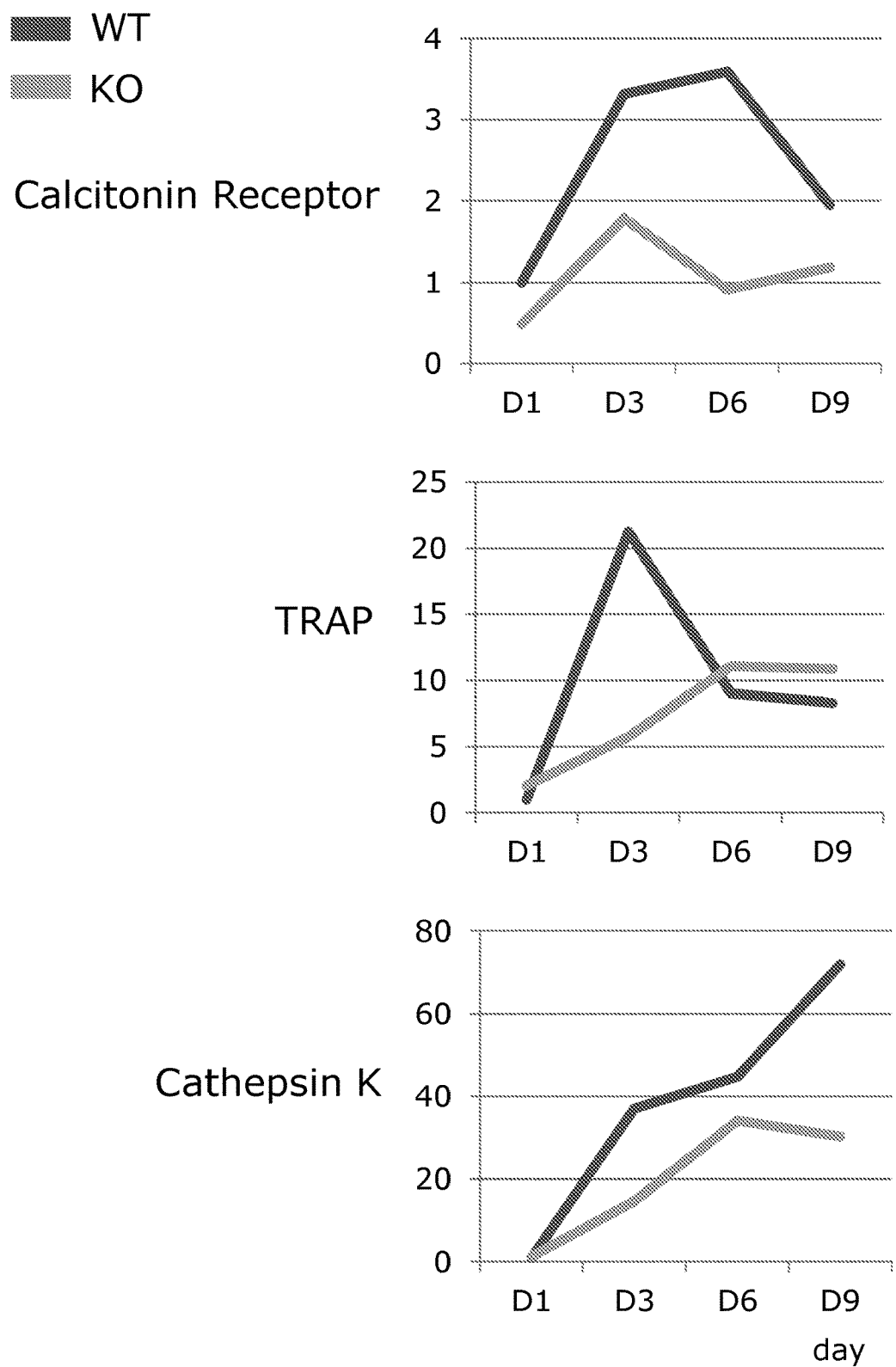
FIGS. 3A and 3B: Increased expression of sialoadhesin during osteoclastogenes is necessary for normal expression of osteoclast marker proteins. Quantitative RT-PCR analysis on stimulated bone marrow cells at different time points (days) of (FIG. 3A) RNA expression of calcitonin receptor, tartrate-resistant acid phosphatase (TRAP) and cathepsin K in wild-type and Sn-deficient mice.
Figure 3B:
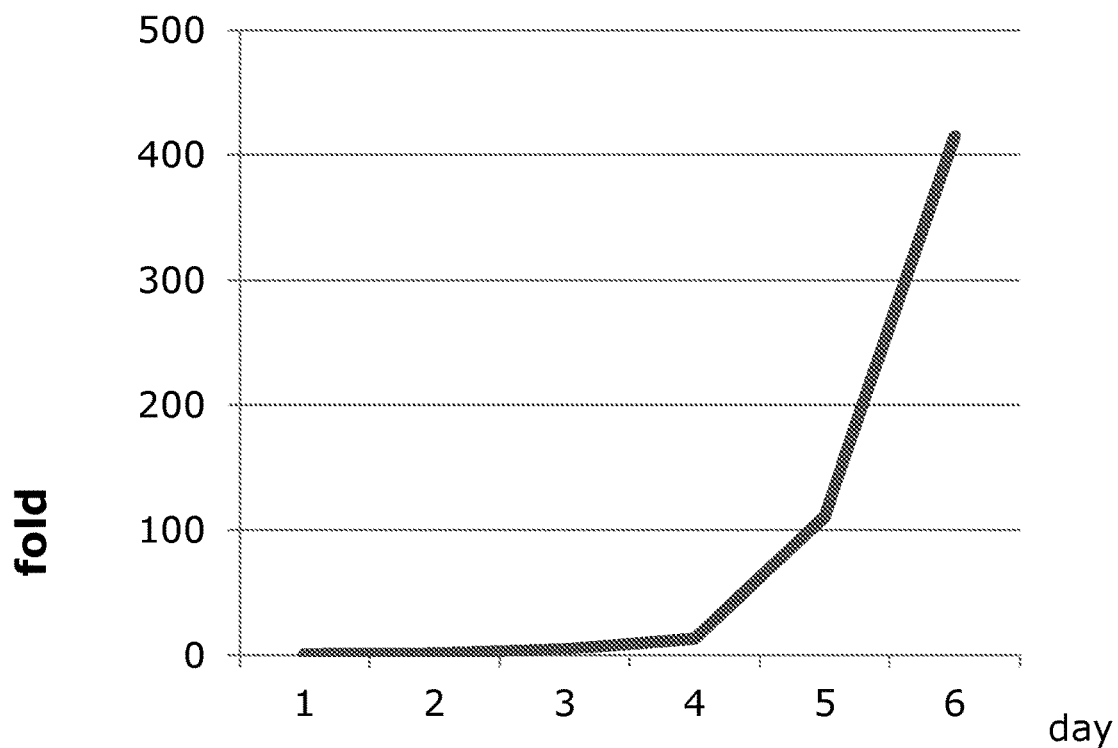

Bone marrow from both non-diseased genotypes was stimulated ex vivo with RANKL and M-CSF to differentiate into osteoclasts. Quantitative RT-PCR was performed on RNA from bone marrow cells at different time points during differentiation. RNA expression of osteoclast marker proteins calcitonin receptor, tartrate-resistant acid phosphatase (TRAP) and cathepsin K was disturbed and decreased at certain time points in Sn-deficient mice (FIG. 3A). As RNA expression of sialoadhesin itself is highly increasing during osteoclast differentiation in wild-type mice, these data implicate a role for sialoadhesin in osteoclastogenesis (FIG. 3B).

Indeed, quantification of TRAP-positive osteoclasts after nine days of differentiation shows less multinucleated or fusing osteoclasts formed from Sn-deficient bone marrow than from wild-type bone marrow.

Sialoadhesin Deficiency Impedes Bone Erosion in a CIA Mouse Model.

Wild-type and sialoadhesin (Sn) knockout mice were immunized with collagen to initiate Collagen-Induced Arthritis (CIA). All mice were clinically scored three times a week until 60 days after immunization on which the mice were sacrificed for further analysis.

Figure 4A:
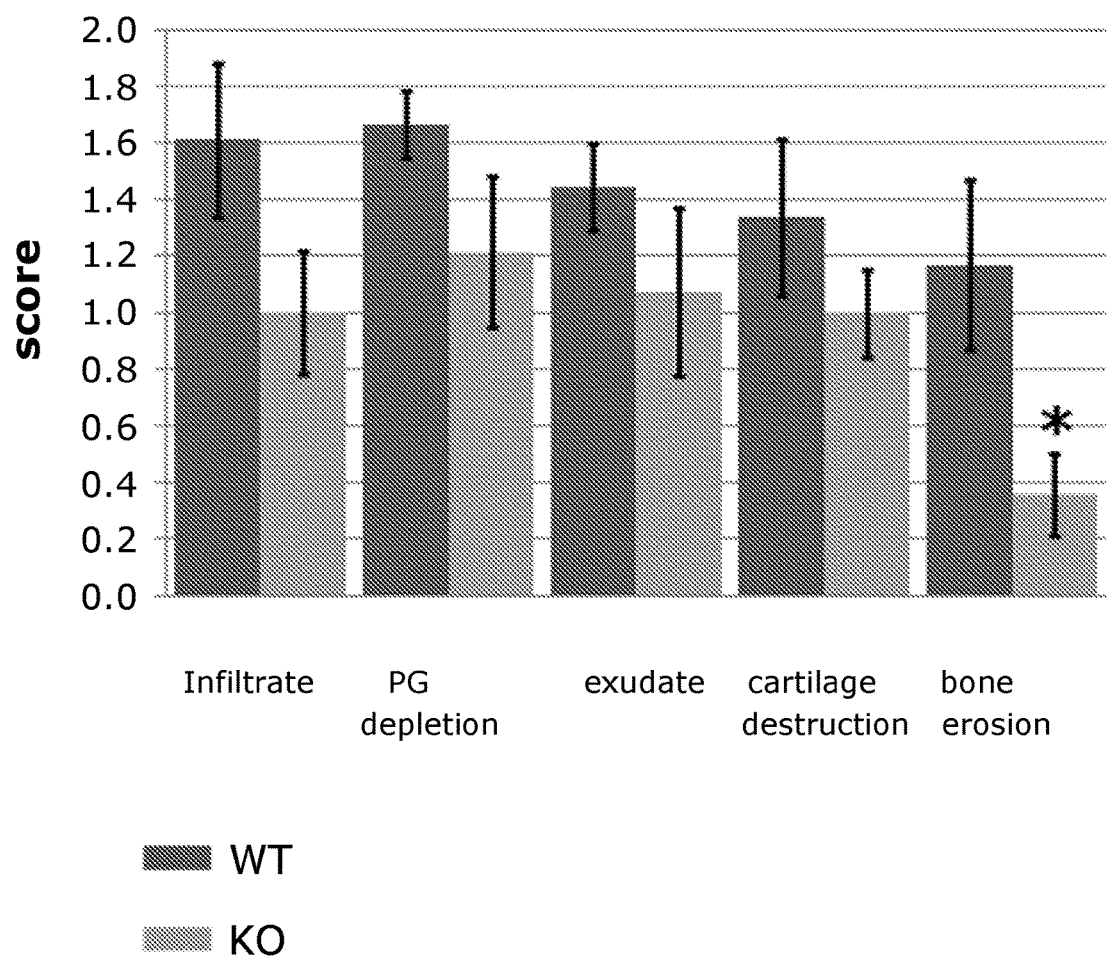
FIGS. 4A and 4B: Sialoadhesin deficiency impedes bone erosion in a CIA mouse model.

Femoropatellar and femorotibial joints were scored for inflammation, exudate, proteoglycan depletion, cartilage destruction and bone erosion. Bone loss was significantly less present in the knee joints of the Sn knockout mice as compared with the normal resulting bone erosion in arthritis in wild-type mice. Strikingly, the difference in bone erosion between both groups was clearly more pronounced than the difference in the other parameters as only the scores for bone erosion were significantly different, but not inflammation, exudate, proteoglycan depletion and cartilage destruction (FIG. 4A).

Figure 4B:
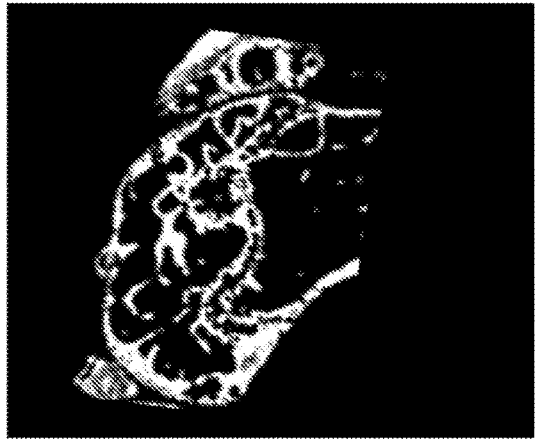
Figure 4B:

The effect on bone was confirmed by microCT as normal bone erosion in a hind paw due to arthritis in a wild-type mouse is clear at the bone surface of femur, patella and tibia at the joint, compared to the smoother surface of a non-diseased wild-type mouse. In contrast, the structure of the bone surface of a-hindpaw of an Sn knockout mouse with arthritis turns out to be less eroded. The bone structure within the femoral condyle and epicondyle is affected more in WT mice then in Sn KO mice, 60 days after arthritis induction (FIG. 4B). Moreover, in a three-dimensional section of the tibia, a thicker trabecular density was noticed in the KO mice than in the WT mice.

Sialoadhesin Deficiency Decreases Bone Degradation in a CAIA Mouse Model.

Figure 5A:
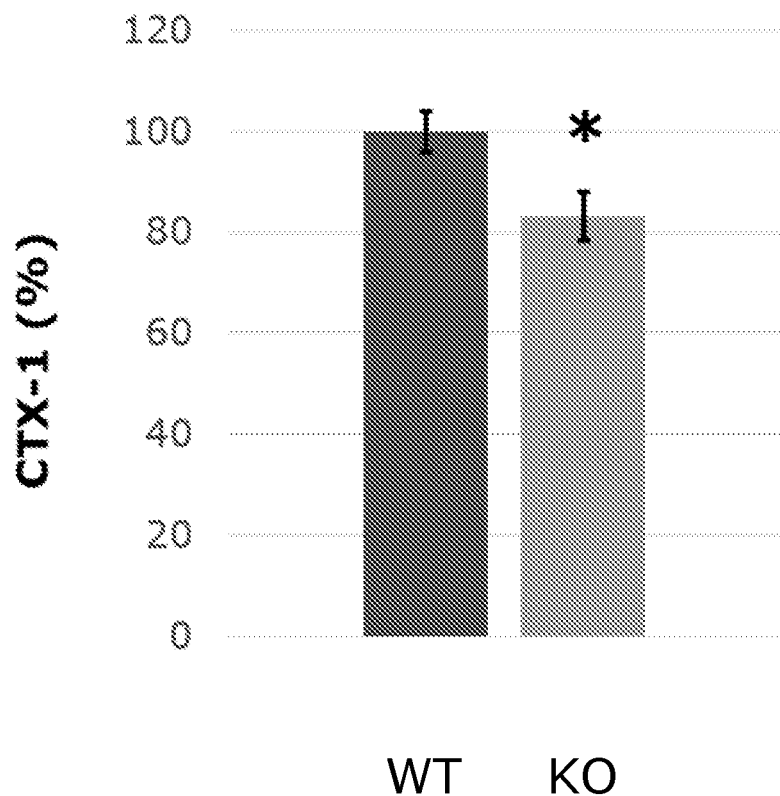
FIGS. 5A and 5B: Sialoadhesin deficiency decreases bone degradation in a CAIA mouse model.
Figure 5B:
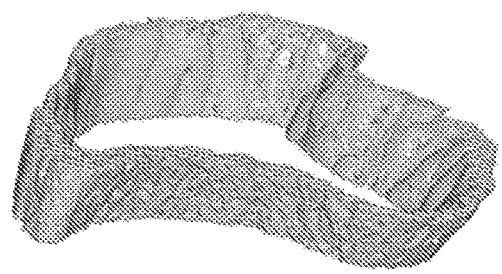
Figure 5B:
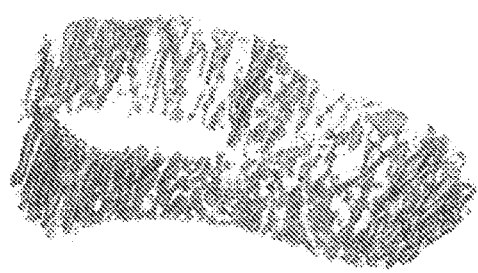
Figure 5B:
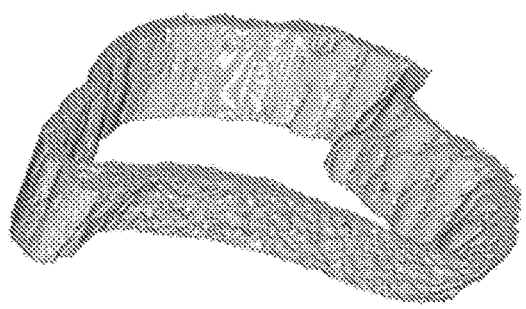
Figure 5B:
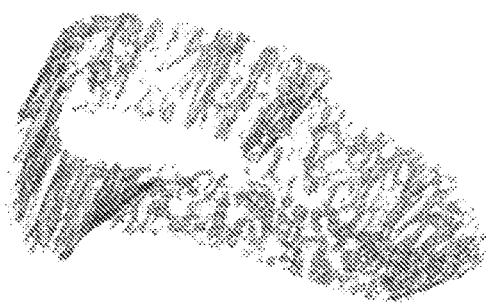

A cocktail of four monoclonal anti-collagen antibodies was administered to both wild-type and sialoadhesin (Sn) knockout mice to develop Collagen Antibody-Induced Arthritis. C-terminal telopeptide of type I collagen (CTX-1), a marker of bone resorption was significantly lower in diseased Sn knockout mice (clinical score ≥3) than in diseased wild-type mice at the peak of the arthritis manifestation (day 9 after induction) (FIG. 5A). The higher bone degradation in wild-type mice was visualized by microCT analysis of a part of tibial cortical bone by filling and measuring the pores in the cortex. Cortical porosity (ratio pores volume/total cortical volume) was 0.081 for the wild-type mouse and 0.061 for the Sn knockout mice, both with the same clinical knee score, shown in FIG. 5B, confirming the effect of sialoadhesin on bone loss.

Sialoadhesin Deficiency Significantly Diminishes the Process of Osteoporosis after Ovariectomy in Mice.

Figure 6A:
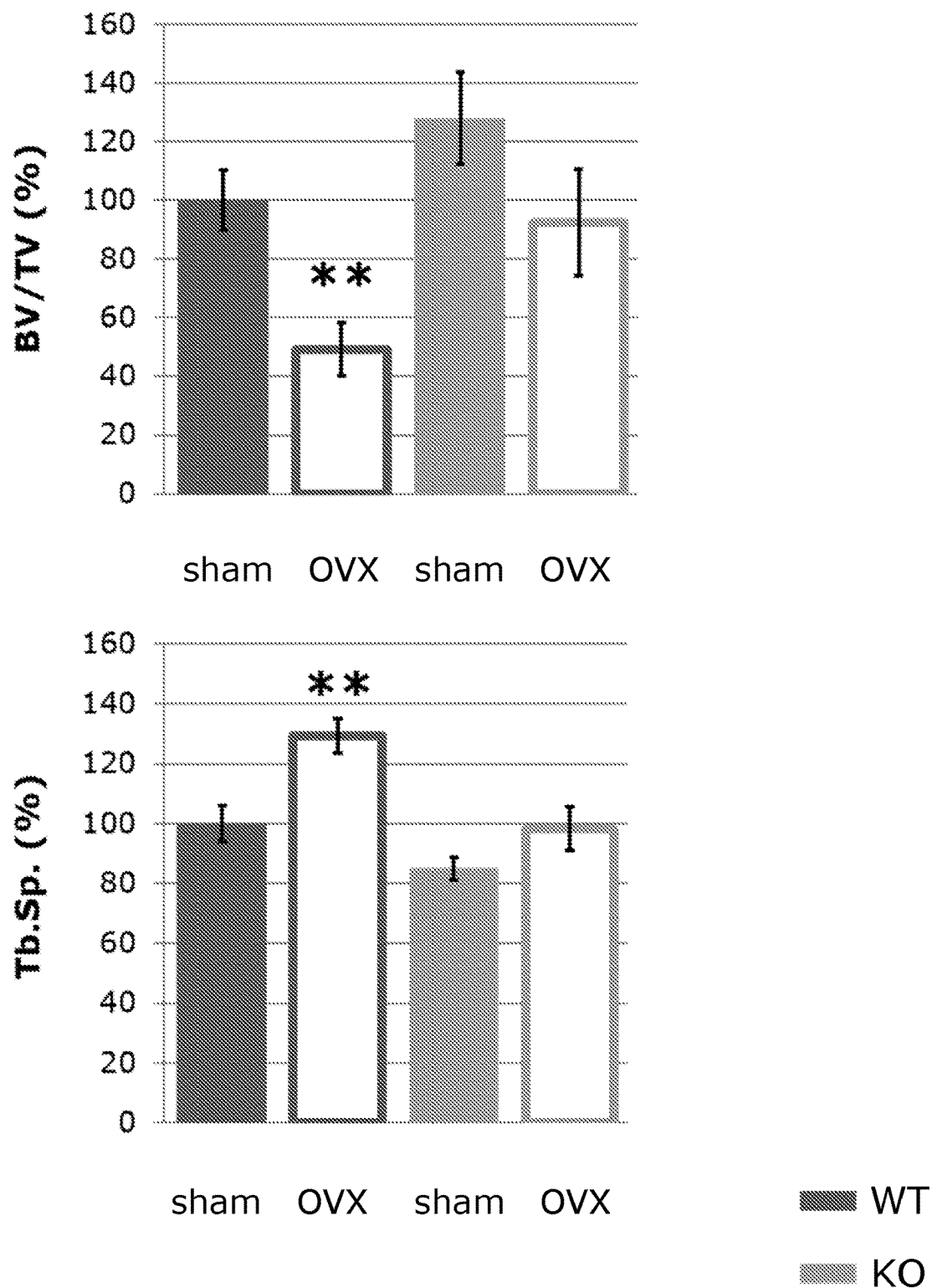
FIGS. 6A and 6B: Sialoadhesin deficiency significantly diminishes the process of osteoporosis after ovariectomy in mice.
Figure 6B:
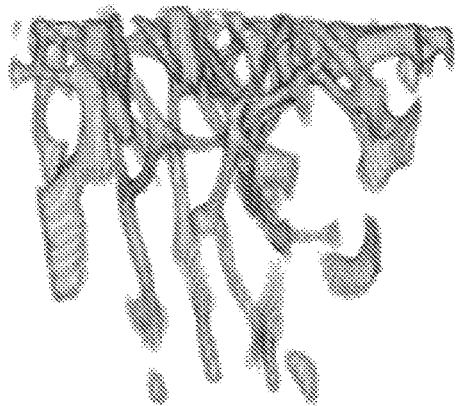
Figure 6B:
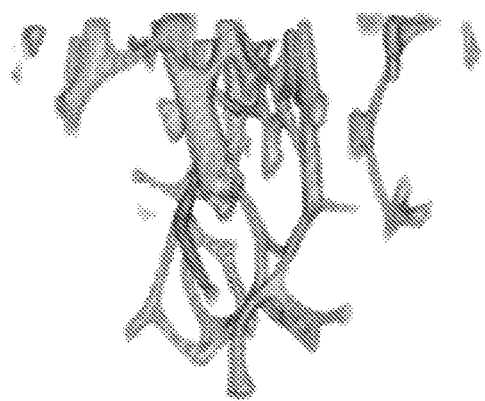
Figure 6B:
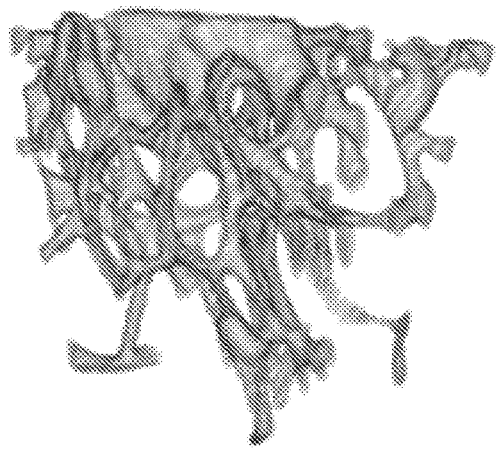
Figure 6B:

A group of both wild-type and sialoadhesin knockout mice were either sham-operated or ovariectomized to experimentally induce the development of postmenopausal osteoporosis during 6 weeks. The established osteoporotic phenotype in wild-type mice that had undergone ovariectomy (OVX) compared to the wild-type sham-operated group was clearly less pronounced in the Sn knockout condition. This was shown by microCT analysis of the tibia and a loss of significance for the difference in trabecular bone volume/total volume and trabecular separation in the knockout mice as compared to the wild-type mice (sham versus ovx) (FIG. 6A). Visualization of the trabecular network of representative mice from each group (FIG. 6B) confirms the effect of sialoadhesin on disease-induced bone loss.

Addition of Anti-Sialoadhesin Antibodies Decrease Ex Vivo Osteoclast Formation and In Vivo Inflammation-Induced Bone Erosion.

Figure 7A:
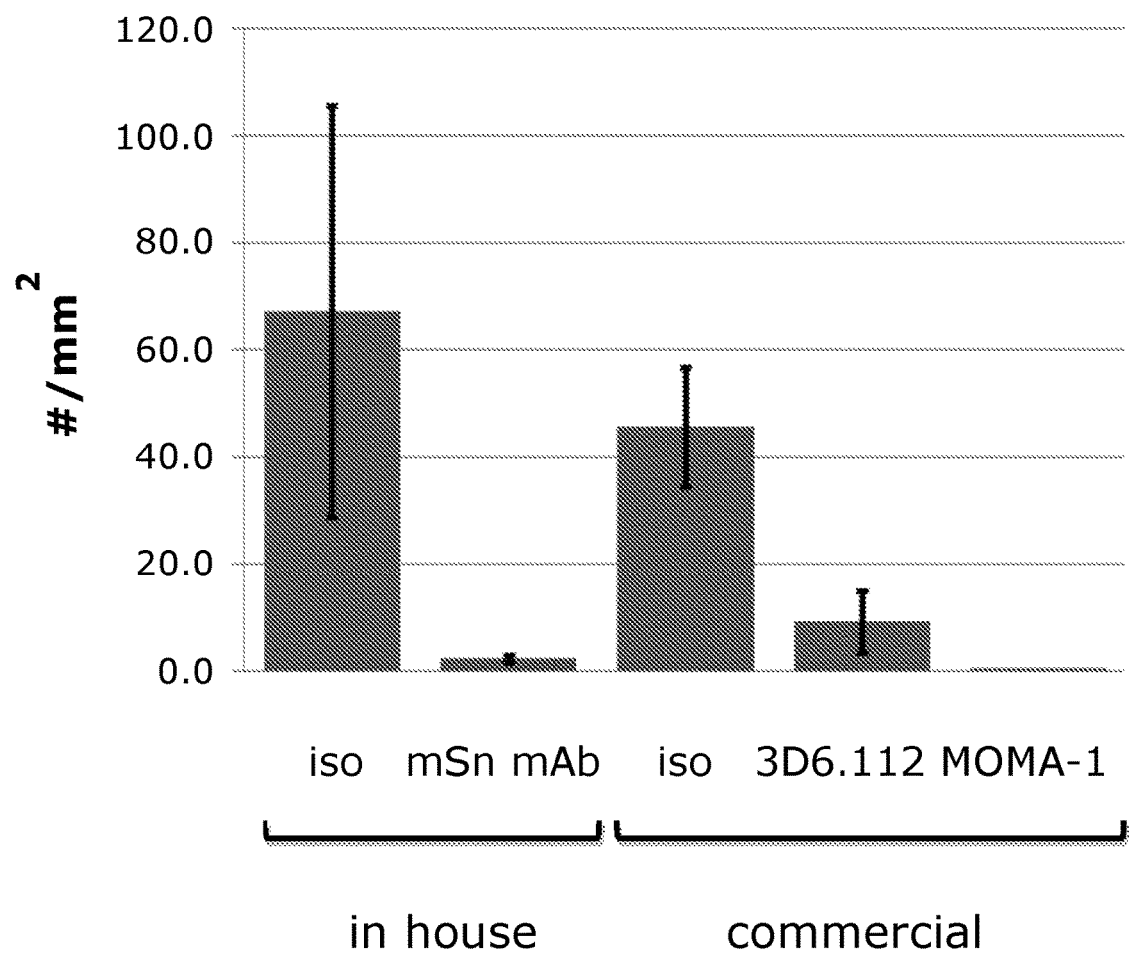
FIGS. 7A and 7B: Anti-sialoadhesin antibodies decrease both ex vivo osteoclast formation and in vivo inflammation-induced bone erosion.

Bone marrow cells from wild-type mice were stimulated with RANKL and M-CSF to differentiate into osteoclasts. After detection of TRAP activity, osteoclasts were quantified. The addition of all three different antibodies against sialoadhesin (an in-house Ab, a commercially available 3D6.112 Ab, or MOMA-1) resulted in a similar dramatic decrease of osteoclast formation compared with their isotype controls (FIG. 7A).

Figure 7B:
Figure 7B:
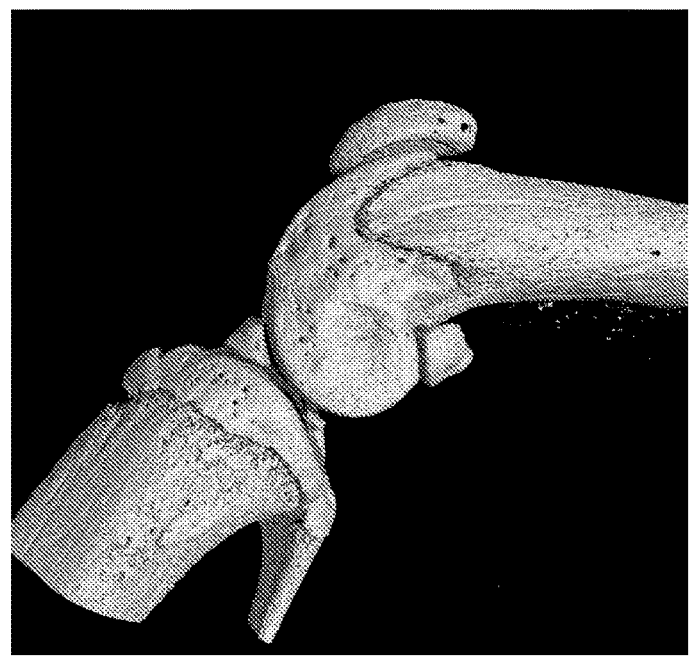

DBA/1 mice were immunized with collagen to initiate collagen-induced arthritis. Fourteen days after immunization, mice were treated twice per week with either PBS or the in-house anti-Sn antibody. All mice were clinically scored at least three times a week until 42 days after immunization. Importantly, microCT revealed less bone erosion in the antibody-treated group than in the PBS-treated group (FIG. 7B).

REFERENCES

Dimitrov, D. S. (2009). Engineered CH2 domains (nanoantibodies). *mAbs* 1:26-28.

Hartnell, A., J. Steel, H. Turley, M. Jones, D. G. Jackson, and P. R. Crocker (2001). Characterization of human sialoadhesin, a sialic acid binding receptor expressed by resident and inflammatory macrophage populations. *Blood* 97:288-296.

Hiruma, Y., T. Hirai, and E. Tsuda (2011). Siglec-15, a member of the sialic acid-binding lectin, is a novel regulator for osteoclast differentiation. *Biochem. Biophys. Res. Commun.* 409(3):424-429.

Hiruma, Y., E. Tsuda, N. Maeda, A. Okada, N. Kabasawa, M. Miyamoto, H. Hattori, and C. Fukuda (2013). Impaired osteoclast differentiation and function and mild osteopetrosis development in Siglec-15-deficient mice. *Bone* 53(1):87-93.

Hughes, J. M. and M. A. Petit (2010). Biological underpinnings of Frost's mechanostat thresholds: the important role of osteocytes. *J. Musculoskelet. Neuronal Interact.* 10(2):128-135.

Ishida-Kitagawa, N., K. Tanaka, X. Bao, T. Kimura, T. Miura, Y. Kitaoka, K. Hayashi, M. Sato, M. Maruoka, T. Ogawa, J. Miyoshi, and T. Takeya (2012). Siglec-15 protein regulates formation of functional osteoclasts in concert with DNAX-activating protein of 12 kDa (DAP12). *J. Biol. Chem.* 287(21):17493-17502.

Kameda, Y., M. Takahata, M. Komatsu, S. Mikuni, S. Hatakeyama, T. Shimizu, T. Angata, M. Kinjo, A. Minami, and N. Iwasaki (2013). Siglec-15 regulates osteoclast differentiation by modulating RANKL-induced phosphatidylinositol 3-kinase/Akt and Erk pathways in association with signaling Adaptor DAP12. *J. Bone Miner. Res.* 28(12):2463-2475.

Kim, S. H. and S. H. Moon (2008-2012). Osteoclast differentiation inhibitors: a patent review. *Expert Opin. Ther. Pat.* 23(12):1591-1610.

Nakashima, T., M. Hayashi, T. Fukunaga, K. Kurata, M. Oh-Hora, J. Q. Feng, L. F. Bonewald, T. Kodama, A. Wutz, E. F. Wagner, J. M. Penninger, and H. Takayanagi (2011). Evidence for osteocyte regulation of bone homeostasis through RANKL expression. Nat. Med. 17(10): 1231-1234.

Nath, D., P. A. Vandermerwe, S. Kelm, P. Bradfield, and P. R. Crocker (1995). The amino-terminal immunoglobulin-like domain of sialoadhesin contains the sialic acid binding site. Comparison with CD22. Journal of Biological Chemistry 270:26184-26191.

Oetke, C., M. C. Vinson, C. Jones, and P. R. Crocker (2006). Sialoadhesin-deficient mice exhibit subtle changes in B- and T-cell populations and reduced immunoglobulin M levels. *Mol. Cell. Biol.* 26(4):1549-1557.

Stuible, M., A. Moraitis, A. Fortin, S. Saragosa, A. Kalbakji, M. Filion, and G. B. Tremblay (2014). Mechanism and function of monoclonal antibodies targeting siglec-15 for therapeutic inhibition of osteoclastic bone resorption. *J. Biol. Chem.*, Mar. 7, 2014; 289(10):6498-6512.

Takahata, M., N. Iwasaki, H. Nakagawa, Y. Abe, T. Watanabe, M. Ito, T. Majima, and A. Minami (2007). Sialylation of cell surface glycoconjugates is essential for osteoclastogenesis. *Bone* 41(1):77-86.

Tramontano, A., E. Bianchi, S. Venturini, F. Martin, A. Pessi, and M. Sollazzo (1994). The making of the minibody: an engineered beta-protein for the display of conformationally constrained peptides. *J. Mol. Recognition* 7:9-24.

Vanderheij den, N., P. L. Delputte, H. W. Favoreel, J. Vandekerckhove, J. Van Damme, P. A. van Woensel, and H. J. Nauwynck (2003). Involvement of sialoadhesin in entry of porcine reproductive and respiratory syndrome virus into porcine alveolar macrophages. *Journal of Virology* 77:8207-8215.

Vinson, M., P. A. van der Merwe, S. Kelm, A. May, E. Y. Jones, and P. R. Crocker (1996). Characterization of the sialic acid-binding site in sialoadhesin by site-directed mutagenesis. *J. Biol. Chem.* 271:9267-9272.

Vlassenbroeck J, M. Dierick, B. Masschaele, V. Cnudde, L. Van Hoorebeke, and P. Jacobs (2007). *Instruments and Methods in Physics Research Section A. Accelerators, Spectrometers, Detectors and Associated Equipment* 580: 442-445. Software tools for quantification of X-ray microtomography at the UGCT; Nuclear, Yagi, M., T. Miyamoto, Y. Sawatani, K. Iwamoto, N. Hosogane, N. Fujita, K. Morita, K. Ninomiya, T. Suzuki, K. Miyamoto, Y. Oike, M. Takeya, Y. Toyama, and T. Suda (2005). DC-STAMP is essential for cell-cell fusion in osteoclasts and foreign body giant cells. *J. Exp. Med.* 202(3):345-351.

Xiao, H., L. Shan, H. Zhu, and F. Xue (2012). Detection of significant pathways in osteoporosis based on graph clustering. *Mol. Med. Rep.* Dec. 6, 2012 (6):1325-32.

Xiong, J., M. Onal, R. L. Jilka, R. S. Weinstein, S. C. Manolagas, and C. A. O'Brien (2011). Matrix-embedded cells control osteoclast formation. *Nat. Med.* 17(10):1235-41.

Zhang, C., C. Dou, J. Xu, and S. Dong (2014). DC-STAMP, the Key Fusion-Mediating Molecule in Osteoclastogenesis. *J. Cell. Physiol.* Jan. 13, 2014. doi: 10.1002/jcp.24553. [Epub ahead of print]

The invention claimed is:

1. A pharmaceutical composition comprising:
   an antibody that specifically binds sialoadhesin (Sn);
   an agent for treating bone disorders in an amount useful for the treatment of a bone loss disorder or bone loss disorders in the subject; and
   a pharmaceutically acceptable carrier and/or excipient.

2. The pharmaceutical composition of claim 1, wherein the antibody antagonizes sialoadhesin-mediated osteoclast fusion.

3. The pharmaceutical of claim 1, wherein the agent for treating bone disorders is selected from the group consisting of estrogens, selective estrogen receptor modulators, alendronate, risedronate, calcitonin, parathyroid hormone, Teriparatide, RANKL inhibitors, cathepsin K inhibitors, integrin inhibitors, src inhibitors, V-ATPase inhibitors, bafilomycin; zoledronic acid, clodronate, tiludronate, pamidronate, etidronate, ibandronate, partial estrogen agonists and antagonists, genistein, daidzein and related phytoestrogens, tamoxifen, bone binding transition metals gallium, thallium, and indium, and inhibitors of chloride channel activity.

4. A pharmaceutical composition comprising:
   an antibody that specifically binds sialoadhesin (Sn);
   an agent for treating bone disorders; and
   a pharmaceutically acceptable carrier and/or excipient.

5. The pharmaceutical of claim 4, wherein the agent for treating bone disorders is selected from the group consisting of estrogens, selective estrogen receptor modulators, alendronate, risedronate, calcitonin, parathyroid hormone, Teriparatide, RANKL inhibitors, cathepsin K inhibitors, integrin inhibitors, src inhibitors, V-ATPase inhibitors, bafilomycin; zoledronic acid, clodronate, tiludronate, pamidronate, etidronate, ibandronate, partial estrogen agonists and antagonists, genistein, daidzein and related phytoestrogens, tamoxifen, bone binding transition metals gallium, thallium, and indium, and inhibitors of chloride channel activity.

* * * * *

UNITED STATES PATENT AND TRADEMARK OFFICE
CERTIFICATE OF CORRECTION

PATENT NO. : 10,479,832 B2
APPLICATION NO. : 15/129792
DATED : November 19, 2019
INVENTOR(S) : Dirk Elewaut, Els Louagie and Nele Juchtmans It is certified that error appears in the above-identified patent and that said Letters Patent is hereby corrected as shown below:

In the Specification

In Column 4, Line 5, please replace "femural" with --femoral--

In Column 13, Line 6, please replace "biopts" with --biopsies--

In Column 15, Line 43, please replace "pheripheral" with --peripheral--

In Column 16, Line 49, please replace "femural" with --femoral--

In Column 18, Line 43, please replace "Vanderhij den" with --Vanderheijden--

Signed and Sealed this
Fourteenth Day of January, 2020

Andrei Iancu
*Director of the United States Patent and Trademark Office*